United States Patent

Mahoney et al.

[11] Patent Number: 6,023,008
[45] Date of Patent: Feb. 8, 2000

[54] WOUND DRESSING, MANUFACTURE AND USE

[75] Inventors: Peter M.J. Mahoney, Powys; David Kershaw, Gwent, both of United Kingdom

[73] Assignee: Bristol-Myers Squibb Company, New York, N.Y.

[21] Appl. No.: 08/765,878

[22] PCT Filed: Jul. 11, 1995

[86] PCT No.: PCT/EP95/02691

§ 371 Date: May 30, 1997

§ 102(e) Date: May 30, 1997

[87] PCT Pub. No.: WO96/01659

PCT Pub. Date: Jan. 25, 1996

[30] Foreign Application Priority Data

Jul. 11, 1994 [GB] United Kingdom .................. 9413932

[51] Int. Cl.[7] ...................................................... A61F 5/00
[52] U.S. Cl. .............................. 602/56; 602/41; 602/58
[58] Field of Search .................................. 602/41, 58, 56

[56] References Cited

U.S. PATENT DOCUMENTS 5,681,579  10/1997  Freeman .................................. 424/448

FOREIGN PATENT DOCUMENTS

0 279 118 B1   4/1986   United Kingdom.
97/07758       3/1997   WIPO.

*Primary Examiner*—John G. Weiss
*Assistant Examiner*—Kelvin Hart
*Attorney, Agent, or Firm*—John M. Kilcoyne; Theodore R. Furman, Jr.

[57] ABSTRACT

An autoadhesive wound dressing which having a pad of highly absorbent alginate fibers, one face of which is provided with an interrupted layer of a pressure sensitive adhesive. Such a dressing has the advantages that a separate dressing need not be used to secure the autoadhesive dressing and the autoadhesive dressing may be cut to fit an irregular wound.

9 Claims, 5 Drawing Sheets

Fig. 2 TGA

WOUND DRESSING, MANUFACTURE AND USE

This invention relates to wound dressings, their manufacture and use. More particularly, this invention relates to wound dressings comprising an alginate pad and an adhesive layer, to the method of their manufacture by applying a water based adhesive to an alginate pad and to the use of such dressings in treating wounds.

A number of alginate wound dressings are available comnercially. Alginate dressings have the virtue of being able to absorb significant amounts of wound exudate and help maintain the wound in a condition which aids its recovery. It is frequently desirable to render the dressing autoadhesive by which it is meant that it can be located at the wound without reliance on a separate dressing. Because of the need to maintain the absorptive properties of the dressing and because of difficulties in applying adhesives directly to known forms of alginate pads, the art has hitherto achieved autoadherence by providing the dressing with a peripheral flange which is coated with adhesive; for example as described in European Patents 243,069 and 236,104. Such dressings locate the alginate pad over the wound by adhering to the skin surrounding the wound. They are rather difficult to manufacture and are not easily cut to shape when i. is desired to match the dressing to the shape of an irregular wound.

A dressing has now been discovered which is absorbent, autoadhesive, capable of being manufactured without recourse to peripheral adhesive coated flanges and which can be cut to shape if desired. Hitherto it has not been practical to provide alginate dressings with adhesive on the alginate itself because of processing difficulties and, more importantly, the relatively poor absorption properties that resulted.

Accordingly the present invention provides an autoadhesive wound dressing which comprises a pad of highly absorbent alginate fibres one face of which has an interrupted layer of a pressure sensitive adhesive.

By "highly absorbent" with respect to the fibre it is meant that they will absorb at least 40 g/g of deionized water. A suitable method of determination is set forth hereinafter. Most aptly the alginate fibres will be present in a pad that can absorb at least 60 times, more aptly at least 80 times, for example 80–280 times its own weight, more aptly 90 to 150 times for example about 120 times its own weight of deionized water.

It is the highly absorbent nature of the pad made from such fibres that allows easy manufacture of the dressing. Previously alginate fibre pads have proved extremely difficult to provide with an adhesive layer but by using a water based adhesive in conjunction with such a highly absorbent fibres a dressing with particularly desirable properties has been produced.

Because of their highly absorbent nature, the dressings of this invention are particularly suitable for use on exuding wounds such as ulcer, burns or the like. When used to treat such wounds the dressing may be cut to shape if desired and gently adhered to the surrounding skin. The dressing can be left in place for a considerable time as it promotes a healthy wound healing environment.

Typically the pad is a wet-laid pad of fibres which if desired can be needle-tacked or hydraulically entangled. miner amounts of fibres of other material may also be present if desired but this is not generally preferred. Most aptly the pad is 0.5 to 7.5 mm thick and is preferably 1 to 5 mm thick, for example 1.5 to 3 mm thick. Typical dressing sizes are rectangular with sides of from 4 to 20 cm, for example 5×15 cm, 10×10 cm and the like although other shapes may be employed, for example circular, oval or the like.

The adhesive employed may be any suitable pressure sensitive adhesive such as a polyacrylate, polyether, polyurethane or the like. Preferably the adhesive layer is derived from an aqueous based adhesive, for example an emulsion adhesive such as aqueous polyacrylate emulsion adhesive.

The adhesive layer will be interrupted, that is it wil have apertures sufficient to permit the passage of exudate there through. The apertures may be in the nature of pores or of perforations, for example associated with fibres penetrating the adhesive layer, in which case a large number of such perforations spaced over the surface of the dressing are most apt, or the apertures may be in the regular pattern produced by using an adhesive layer that results from a printing or pattern spraying process.

One favoured aspect of this invention provides a dressing in which the adhesive layer is a porous layer over the whole of the effective area of the dressing.

The present invention provides a process for the preparation of a dressing according to the invention which comprises applying a layer of adhesive to a pad of highly absorbent alginate fibres in a manner which results in the layer becoming interrupted.

Most aptly this method comprises applying a water based emulsion adhesive to the pad. Surprisingly the highly absorbent nature of the fibres allows this process to be put into effect without the need for subsequent drying stages which are energy demanding and which can have a deleterious effect on the fibres.

Most aptly the aqueous emulsion adhesive has a high solids content, for example greater than 50% w/w, more favourably greater than 60% w/w and preferably about 70% w/w.

The aqueous emulsion adhesive may be any skin compatible adhesive but in general it is most suitable to employ a vinyl ether and/or acrylic based adhesive. Preferably the adhesive is an acrylic adhesive and most preferably one which has an anionic type dispersion.

Such adhesives can be specially prepared by the skilled adhesive chemist or may be commercially obtained from adhesive manufacturers. A supplier of emulsion adhesives is BASF.

Suitable apertured layers may be obtained by such methods as applying adhesive all over the surface and allowing or causing apertures to form, for example as is absorbed by the fibres, the resulting layer becomes porous, or by applying in a pattern, for example with a patterned roller or by pattern spraying and the like. Such patterns often allow 10–15% of the surface of the pad to be adhesive free.

Generally the thickness of the adhesive layer will be about 10 to 40 microns, more usually 20 to 30 microns, for example about 25 microns.

If desired the face of the dressing opposite to the adhesive layer may be provided with a film layer, for example as described in WO 90/01954 or EP 0 279 118. The film layer will be a moisture vapour permeable film for example a polyurethane, polyetherester or a polyether amide. Generally the polymers will be hydrophilic, for example as described in EP 0 279 118. Aptly such films will be from 15 to 50 microns thick, more usually 20 to 30 microns, for example 25 microns. The film layer may be applied directly to the surface of the alginate pad but more suitably will be adhered by means of an adhesive, for example as described in WO 90/01954 or EP 0 279 118. Such adhesives are preferably moisture vapour permeable, for example an acrylic, polyurethane or polyether adhesive of which acrylic adhesives are preferred.

The adhesive coated face of the dressing may be provided with a protector in conventional manner, for example a silicone coated release paper may be employed.

The dressing of this invention will preferably be sterile and contained within a bacteria proof pack, for example a sealed pouch comprising for example a conventional paper-plastics film laminate or a paper aluminium foil and plastic film laminate. The dressing may be sterilised within the pack in conventional manner, for example gamma or electron irradiation or ethylene oxide gas.

The preferred fibres employed in fabric according to the invention may be characterised by reference to their unique thermal properties, in that a plot of the first order derivative of percentage weight loss of the fibre with temperature against temperature has two maxima in the range of 100 to 400° C. (Fibres free of adhesive may be obtained by removing some from the top of the dressing or by removing the adhesive for example by treatment with dichloro methane).

In general, the two maxima in the plot of the first order derivative of percentage weight loss with temperature against temperature for a fibre according to the invention will fall within the range 200 to 300° C., preferably 220 to 290° C.

In general, the two maxima in the plot of the first order derivative of percentage weight loss with temperature against temperature for a fibre according to the invention will fall within the range 200 to 300° C., preferably 220 to 290° C.

Thermogravimetric analysis was performed using a 2950TGA manufactured by TA Instruments, Delaware, U.S.A. Differential scanning calorimetry (DSC) was performed using a DSC7 manufactured by Perkin-Elmer.

Figure 1:
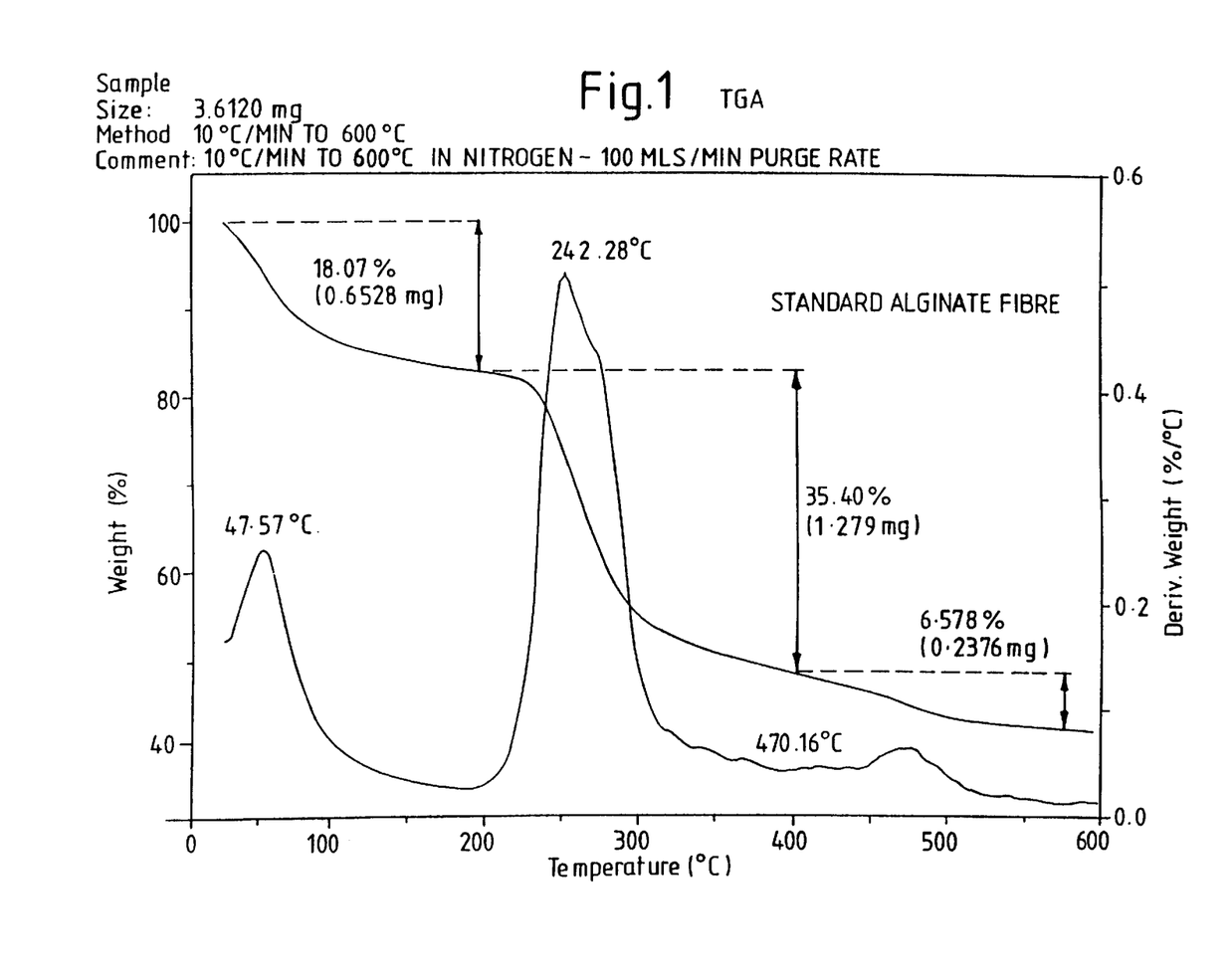
FIG. 1 shows the thermogravimetric analysis (TGA) of an 80:20 calcium:sodium alginate fibre prepared by conventional methods.
Figure 2:
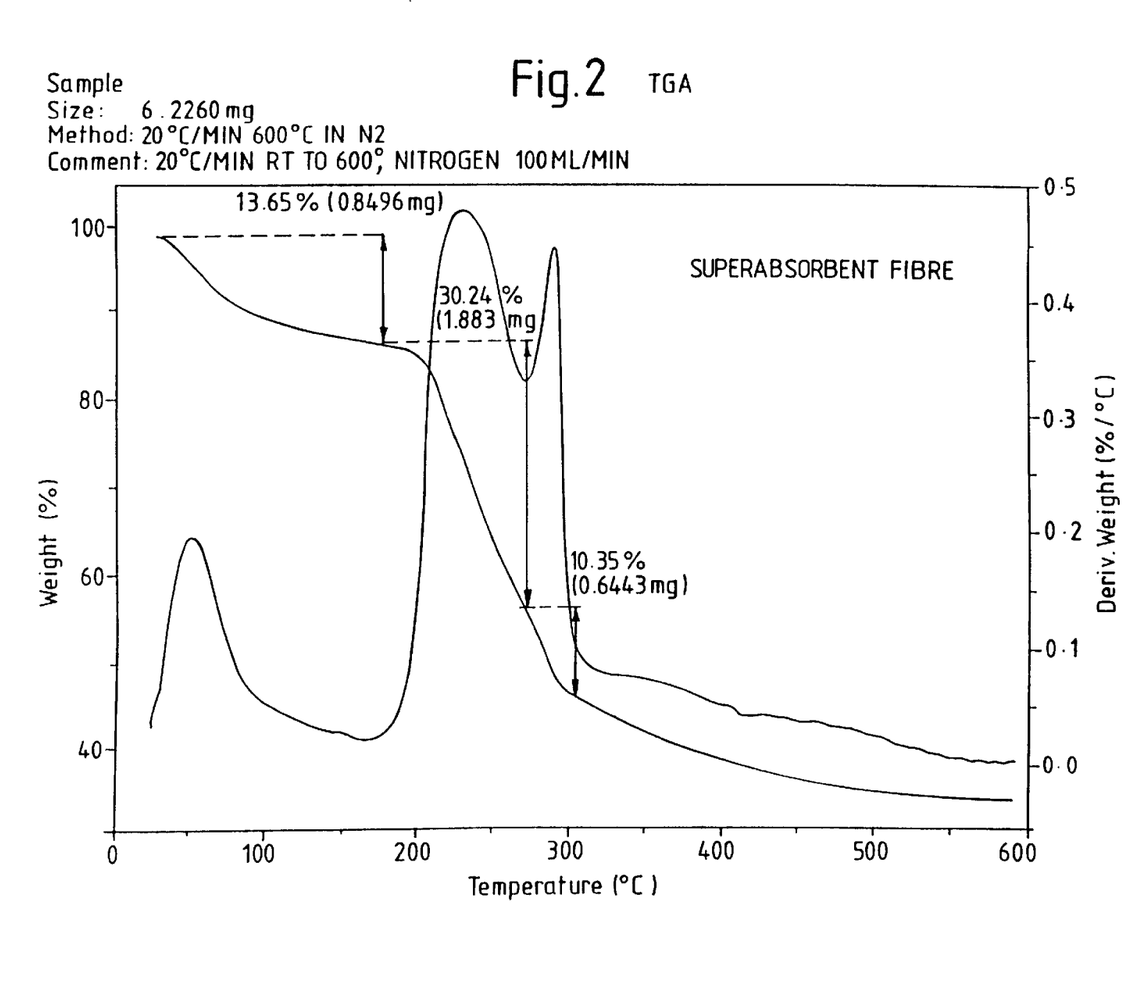
FIG. 2 shows the thermogravimetric analysis (TGA) of a fibre according to the invention, prepared from the same source material as the fibre of FIG. 1.
Figure 3:
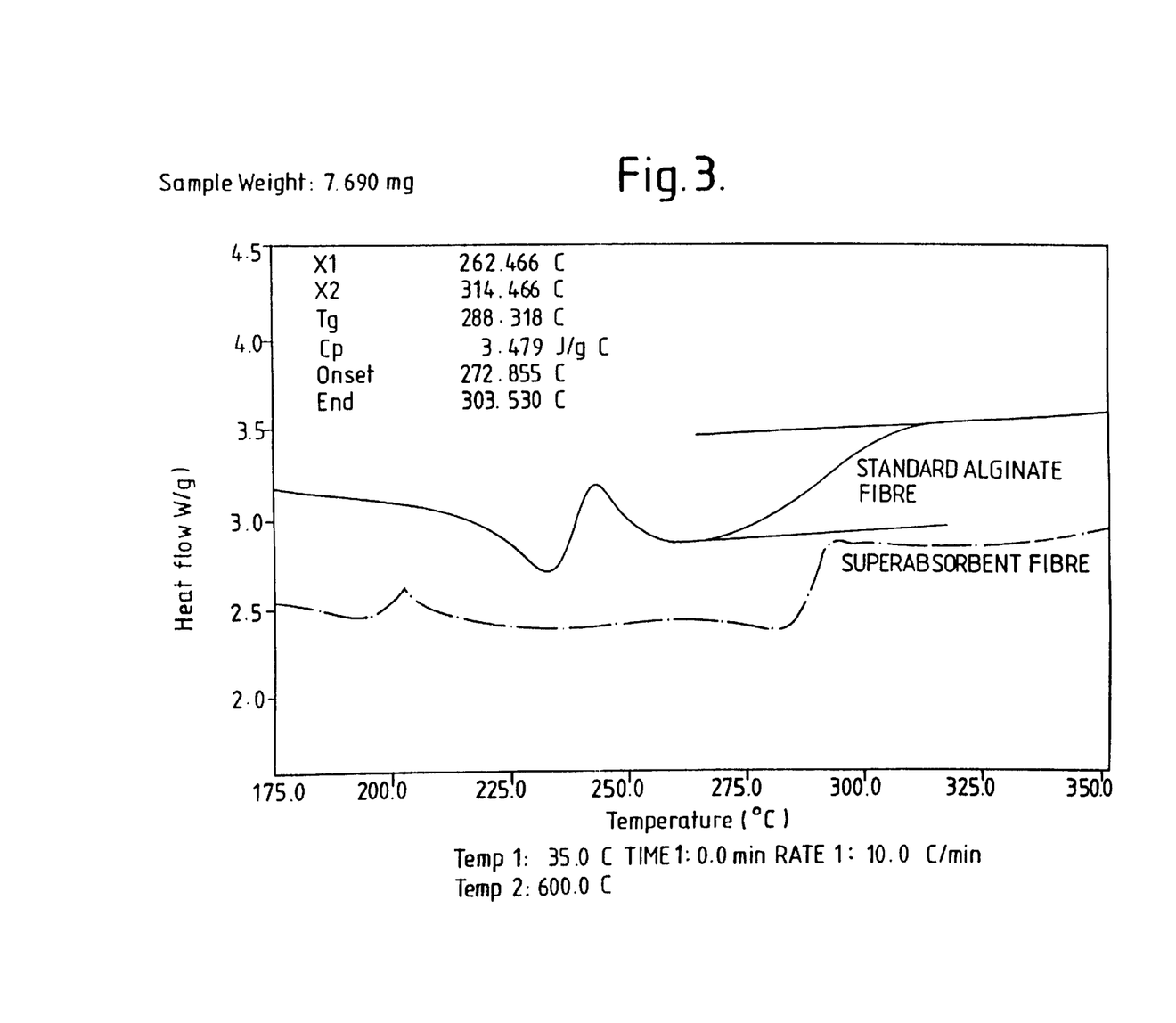
FIG. 3 shows the variation of heat flow with temperature for a conventional 80:20 calcium:sodium alginate fibre and a corresponding fibre in accordance with the present invention.
Figure 4:
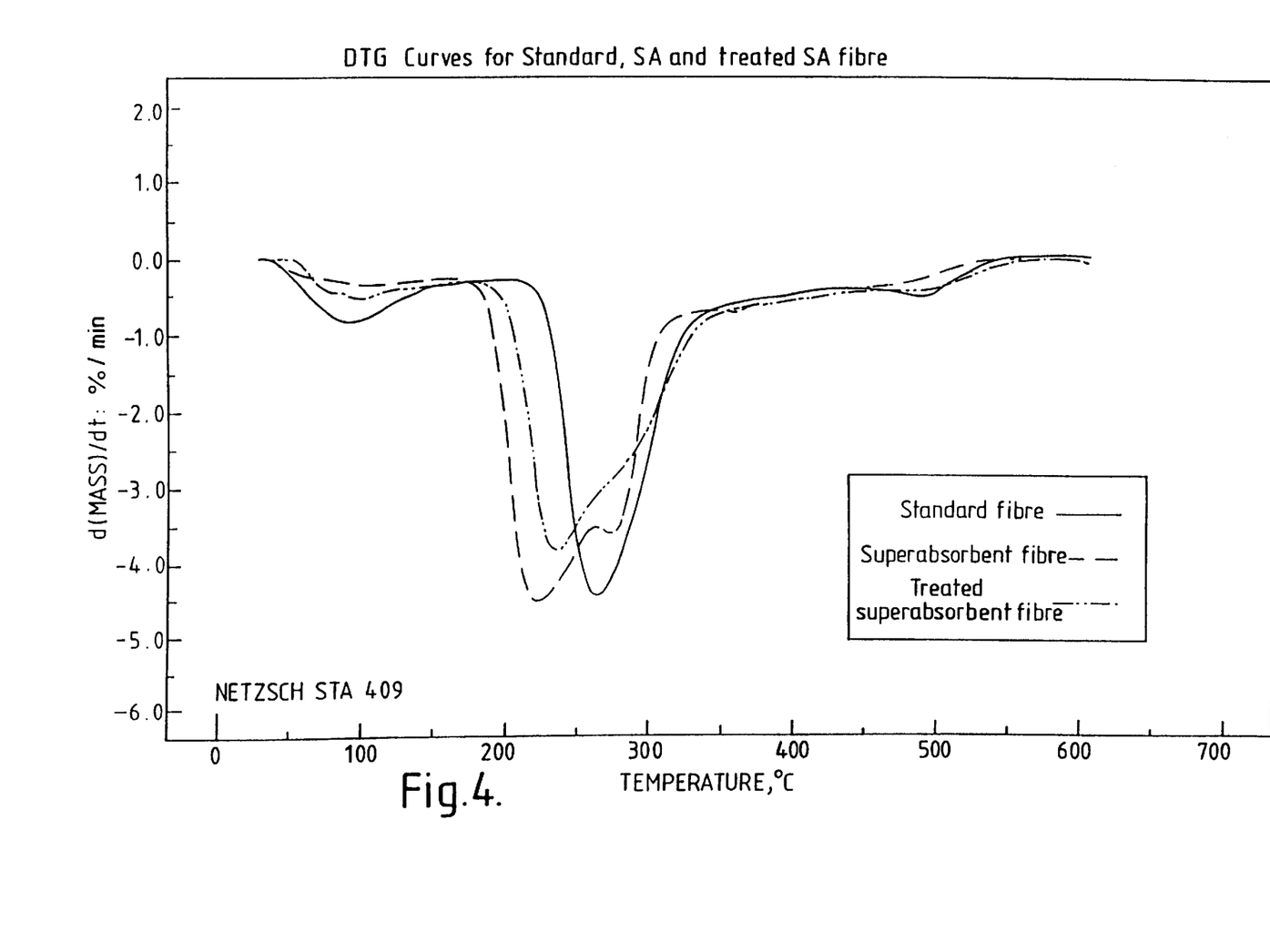
FIG. 4 shows the thermogravimetric analysis of a conventional fibre, a high absorbency fibre according to this invention and such a fibre treated with calcium ions.

It can be seen with reference to FIG. 2, that the first order derivative of percentage weight loss with temperature has two peaks, one at approximately 225° C., and one at a higher temperature approximately 280° C.

Preferred alginate fibres employed in dressings according to the present invention can further be characterised in terms of their glass transition temperature, and in a further or alternative aspect, the present invention thus provides an autoadhesive wound dressing which comprises a pad of alginate fibres on one surface of which is an interrupted layer of adhesive wherein the fabric comprises alginate fibre characterised in that its glass transition temperature is less than 30° C., such as about 26° C.

Figure 5:
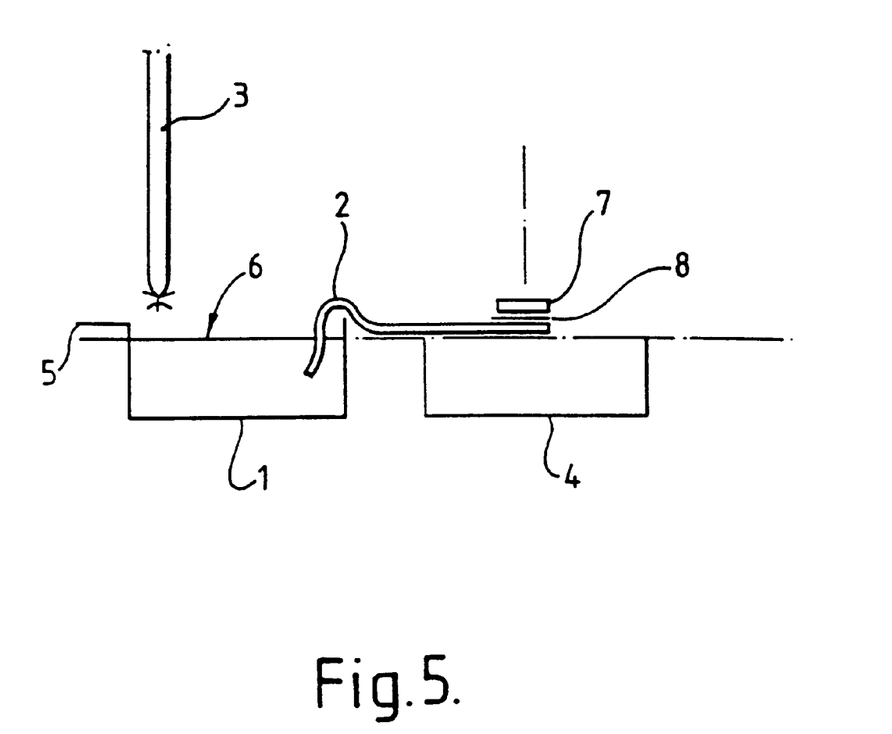

As hereinbefore described preferred alginate fibres employed in dressings of the present invention exhibit improved absorptive properties wherein the absorbency of the fabric is at least 40.0 grams of deionised water per gram of fabric as measured with reference to a test method depicted in FIG. 5 appended hereto.

The alginate pad employed in the dressings of present invention aptly has an absorbency of at least 40 times its own weight of deionised water and more aptly at least 60 times and most aptly at least 80 times its own weight of deionised water. Typically the fabric has an absorbency of much greater than this, for example 80 to 280 times its own weight, more aptly 90 to 150 for example such as about 120 grams of deionised water per gram of pad.

Alginate fibres employed in dressings according to the present invention can further be characterised in terms of their dielectric behaviour. For polymers the dielectric constant is dependent on the ease with which the polymer orientates itself in response to an applied field and this is a function of the structure of the polymer. The constant is most easily expressed in terms of the relationship between the in-phase and out-of-phase components of the dynamic field. This is conventionally expressed as Tan δ. Multiple peaks are normally recorded when measuring Tan δ due to a variety of relaxation phenomena. We have found that alginate fibres suitable for use in the fabrics of the present invention have Tan δ values in the range of less than 1 and up to 15 Hz. Conventional alginate fibres have Tan δ values of from 40 Hz to 7000 Hz.

Preferred alginate fibres suitable for use in a dressing according to the present invention, are typically obtained by a process comprising the following steps:

(1) treating alginate fibres with a suitable acid so as to produce fibres comprising approximately 90–98%, such as 95% –98%, alginic acid fibres;
(2) treating the alginic acid fibres with a saturated aqueous solution of mono- or divalent cations;
(3) washing the fibres with water until imbibition of water by the fibres has effectively ceased;
(4) treating the fibres with a source of a cation capable of forming a water-soluble alginate salt.

The fibres used as starting material in step 1 may be conventional salted alginate fibres (for example sodium, calcium, mixed sodium/calcium fibres produced in conventional manner, for example from 2–10% w/w solutions, for example 4% solution)

Most suitably the alginate fibres for use in step (1) are calcium alginate fibres.

Suitable acids for use in step (1) include acids capable of protonating alginic acid and may include both organic and inorganic acids. Preferably, hydrochloric acid will be used. Preferably the resulting alginic acid fibres have at least 95% of the acid residues in the unsalted form.

Suitable mono- or divalent cations for use in step (2) include solutions of sodium, potassium and magnesium cations. Preferably a pharmaceutically acceptable monovalent cation is used, most preferably a sodium ion.

Step (3) is preferably effected by washing the fibres in a stream of deionised water. Desirably step (3) may be discontinued when swelling has ceased.

Cations capable of forming water-soluble alginate salts include, for example, sodium, potassium, lithium, ammonium and magnesium cations. Preferably the source of a cation capable of forming a water-soluble alginate salt used in step (4) is a source of sodium cations, more preferably sodium carbonate. Other carbonates may be used in like manner to produce the alternative salts.

Small quantities of other ions (for example zinc or silver) may be present in step (4) if desired but generally these may be included in the fibre after completion of step (4) if their presence is required.

A method of treating the product of the above process to include other ions is to treat the product with an aqueous solution of a source of the ions.

The fibres may be collected at the end of step (4) by filtration or other suitable method and may be dried, for example by treatment with a volatile drying agent, such as methyl alcohol, ethyl alcohol, isopropyl alcohol, acetone and the like, and then drying in air. It is one of the advantages of this invention that the highly absorbent fibres may be dried without losing their ability to be highly absorbent when rewetted.

The fibres may have any convenient length, for example a staple length of 0.25 to 25 mm, more usually 0.5 to 15 mm, favourably 1 to 12 mm and preferably 1.5 to 10 mm.

For the most highly absorbent products to be obtained, large amounts of divalent ions such as calcium ions are not added at step (4) or later.

The fibres may be treated with an aqueous solution of a desired ion, for example if it is desired to increase the calcium ion content treatment with a source of calcium ions such as a solution of calcium chloride may be used. In such treated fibres the higher of the two maxima (that generally found within the range 280–300° C.) tends to be reduced to a shoulder on the lower of the two maxima (that generally found with a maximum in the range of 200–250° C.). However, the skilled worker will appreciate that a shoulder represents a second peak and the two peaks may be separately drawn using standard computer aided calculations if desired.

For the most highly absorbent products to be obtained, large amounts of divalent ions such as calcium ions are not added at step (4) or later.

Aptly the fibres have a staple length of 0.25 to 25 mm, mnore usually 0.5 to 15 mm, favourably 1 to 12 mm and preferably 1.5 to 10 mm.

The alginate may be obtained from any convenient source, for example L. Hyperborea or Eclonia Maxima of which Eclonia Maxima is preferred.

The fibres prepared according to the above described process may be dried using conventional methods, for example, using acetone or hot air drying.

Alginate pads used in the present invention may have medicaments incorporated therein. Suitable medicaments include those which aid recovery of wounds, for example an antifungal agent, an antibacterial agent, an angiogenesis promoting agent or the like. Favoured medicaments include antifungal agents such as metronidazole, and antibacterial agents such as chlorhexidine, prepared by treating the fibres with an aqueous solution of the medicament or its salt.

It has further been found that hyaluronic acid can be incorporated into the alginate fibres of the fabrics according to the present invention.

A suitable average molecular weight range for HA for use in the dressings of the present invention is $1.5 \times 10^3$ to $2 \times 10^6$, more preferably about $7.5 \times 10^4$.

Incorporation of HA into the alginate fibres may be achieved by contacting alginate fibres with an aqueous solution of HA followed by a suitable aqueous ionic solution, such as a solution of calcium, magnesium or zinc cations, preferably a solution of calcium cations, more preferably aqueous calcium chloride solution.

Alginates are produced by a variety of micro-organisms and marine algae which are the normal commercial source. The alginates being natural materials show considerable variety but are characterised in being block copolymers, the individual monosaccharide units being arranged into groups as blocks of mannuronic (M) and guluronic (G) residues. In addition to the repeating blocks each polymer chain can contain a proportion of alternating M and G monosaccharide units.

Suitably alginate fibres employed in the absorbent layer may be high M or high G, typically 60–80% by weight M or G respectively. The alginate fibres may be high absorbent fibres substantially as hereinbefore described.

In the event that a relatively low absorbency product is required some of the solubilising ions (generally sodium) can be replaced by an insolubilising ion such as calcium. This may be achieved by treating the adhesive coated pad with a source of calcium ions such as a solution of calcium chloride. In such treated fibres the higher of the two maxima (that generally found within the range 280–300° C.) tends to be reduced to a shoulder on the lower of the two maxima (that generally found within the range of 200–250° C.). However, the skilled worker will appreciate that a shoulder represents a second peak and the two peaks may be separately drawn using standard computer aided calculations if desired. Thus the present invention also provides an autoadherent dressing which comprises a pad of alqinate fibre which contains calcium ions in addition to sodium ions and which has two TGA maxima as described herein, and a layer of pressure sensitive adhesive.

The alginate fibres according to the invention may also be formed into a dressing using wet-laying techniques such as those conventional in the paper industry. Conventional alginate fibres cannot be wet-laid using conventional papermaking techniques. The ability of the fibres employed in the present invention to be wet-laid by conventional methods represents an important advantage of the present fibres over conventional alginate fibres.

In the preparation of a pad of non-woven fabric, a cotton card may be used to form a web, which may then be cross-lapped, for example with a Garnet Bywater cross-lapper, and then needle punched in a Garnet Bywater needle loom. In the preparation of a pad of woven fabric, the precursor alginate fibres may be carded and then spun into a yarn, which can be woven in a conventional loom. Alternatively, the fibres may be collected in a spinning box, according to the method described in British Patent No. 568177, and woven. In the preparation of a pad of knitted fabric, the fibres can be prepared as a continuous filament yarn, again according to the method described in British Patent No. 568177, which is then knitted on a conventional knitting machine.

The absorbency of fabric according to the invention may be determined according to the following method. The absorbent test sample (strip) may be obtained from fibres prior to coating or from fibres obtained from the dressing.

TEST METHOD

The apparatus used in the determination of absorbency is depicted in FIG. 5, and consists of water bath 1 containing a 0.9% (w/w) deionised water, absorbent strip 2, burette 3, top-pan balance 4 and overflow 5.

The thickness of the absorbent strip 2 is substantially equivalent to that of the dressing 7. The filter paper 8 has substantially the same planar dimensions as the dressing 7, but not necessarily the same thickness.

The apparatus is set up with the surface 6 of the saline solution or water level with the top surface of the top-pan balance 4. The flow of liquid from the burette 3 is then adjusted to approximately 1.5 ml per minure. The absorbent strip 2 is then saturated and placed between the bath 1 and the balance 4, as depicted in FIG. 2. The balance 4 is then tared. A weighed dressing 7 and filter paper 8 (cut to size) is positioned as depicted in FIG. 2. Care must be taken to ensure that the edge of the absorbent strip 2 furthest away from the water bath 1 does not extend beyond the corresponding edge of the dressing 7, as shown in FIG. 2.

After six minutes the weight shown on the balance 4 is recorded. The dressing 7 and filter paper 8 are then removed and any residual weight on the balance 4 noted.

Absorbency is determined on the basis of the following equation:

$$\begin{matrix}\text{Weight of}\\\text{liquid}\\\text{absorbed}\end{matrix} = \begin{matrix}\text{total weight}\\\text{on balance}\end{matrix} - \left[\begin{matrix}\text{dry}\\\text{weight of}\\\text{dressing}\end{matrix} + \begin{matrix}\text{weight of}\\\text{saturated}\\\text{filter}\\\text{paper}\end{matrix} + \begin{matrix}\text{residual}\\\text{weight on}\\\text{balance}\end{matrix}\right]$$

TEST METHOD 2

The Tan δ value of a fibre was determined by using a Thurlby Thandor TG502 sweep/function generator, a Teczronics 2212 digital storage oscilloscope and a capacitance test cell (plate area 16 square centimetres and fitted with a 22KΩ resistor). The material to be tested was placed in a small engineers vice and the vice closed. The distance between the plates was measured using a vernier calliper and the earth connection made between the vice and the earth terminal of the capacitance test cell. The function generator and oscilloscope were then connected and the amplitude of the applied sinusoidal voltage measured together with the voltage drop across the resistor and the phase angle between the applied voltage signal and current. The frequency of the applied field was then altered and the measurements repeated for many points in the range 5 mHz to 5 MHZ.

DESCRIPTION 1

Calcium alginate fibre (4 g) (spun from 2–8% w/w, 4, 5 or 6% w/w, solution) was immersed in 1M hydrochloric acid (1 1) for 20–30 seconds. The degree of acid conversion was determined from the relative intensities of the peaks at 1720 $cm^{-1}$ and $1600^{-1}$ in the infrared spectrum, to ensure that the degree of conversion was in excess of 95%. The fibre was then washed with water and immersed in saturated saline solution (2 1). The fibre was then chopped to the required staple length. After cutting to the appropriate length the fibre was dispersed into a stirred vessel containing deionised water (2 1). The fibres were washed in a stream of running water until they swelled to their maximum extent and no sodium chloride could be detected in the eluent. Sodium carbonate solution (0.1 M) was then added in 1 ml aliquots whilst monitoring the pH and conductivity of the medium. Care was taken to ensure that the pH did not exceed 6.5. After the addition of approximately 12 mls of sodium carbonate solution (conductivity meter reading between 180 and 200 micro siemens), the material was filtered and dried with acetone followed by air drying.

DESCRIPTION 2

Fibre (14g) produced according to Description 1 were suspended in deionized water (800 $cm^2$) and stirred. A 100 mesh nylon gauze disc was placed in the bottom of a Buchner funnel (diameter 24 $cm^2$) and placed on top of a Buchner flask attached to a vacuum pump. The fibre suspension was poured into the funnel and the water allowed to drain from the pad. Vacuum was applied to remove the remaining water and then released. Isopropanol (approximately 150 ml) was poured gently on to the fibre pad and allowed to freely drain through the structure after which vacuum was applied to remove residual solvent. The pad was dried in an oven at 50° C. to constant weight.

EXAMPLE 1

An alginate fibre pad (10cm ×10 cm) prepared according to Description 1 was spread with an aqueous emulsion polyacrylate adhesive (Acronal V205, 70% solids) using a doctor knife to give a thin uniform layer. The adhesive layer was allowed to dry in air and was then covered by a release paper sheet. The resulting dressing was highly absorbent and capable of adhering to skin and absorbing exudate.

(Acronal is a trade mark of BASF; Acronal V205 has a solids content of 69±1%, a viscosity of 800–1600 mPas at 23° C. shear gradient $2505^1$, a mean particle size of about 0.6 microns, the dispersion type is anionic).

EXAMPLE 2

An alginate fibre pad as described in Example 1 was placed on the adhesive coated side of an adhesive coated polyurethane film (both fibre and adhesive layers approximately 20-20 micron thick). To the exposed surface of the pad was applied an adhesive as described in Example 1 which was subsequently covered with a release layer.

EXAMPLE 3

Example 1 was repeated using Lutonal M42 in place of Acronal. Lutonal M42 is a polyvinyl methylether.

EXAMPLE 4

Tan δ values were measured according to Test Method 2 above for a range of fibre samples. The results were as follows:

| Fibre | Peak 1 Hz | Peak 2 Hz | Peak 3 Hz |
| --- | --- | --- | --- |
| KALTOSTAT[1] | 6449 | 1000 | 896 |
| KALTOGEL[2] | 578 | 416 | 46 |
| KALTOSTAT acid treated, neutralised and dried. | 2929 | 541 | 54 |
| Fibre prepared as in Description 1. | 0.056 | 0.018 | — |

[1] commercially available calcium sodium alginate of high guluronate content
[2] commercially available calcium sodium alginate of high malluronate content

We claim:

1. An autoadhesive wound dressing which comprises a pad of highly absorbent alginate fibres, wherein the alginate fibres have an absorbency of at least 40 g of deionized water per gram of pad, one face of which pad is provided with an interrupted layer of a pressure sensitive adhesive, wherein the alginate fibres are characterised by having a split maxima in the range of 100° C. to 400° C. in a plot of the first order derivative of percentage weight loss of the fibre with temperature against temperature.

2. An autoadhesive wound dressing as claimed in claim 1 wherein the pad comprises alginate fibres which are characterised by having two maxima in the plot of the first order derivative of percentage weight loss with temperature against temperature in the range of 200° C. to 300° C.

3. An autoadhesive wound dressing as claimed in claim 1 wherein the alginate fibres are characterised by having a glass transition temperature of less than 30° C.

4. An autoadhesive wound dressing as claimed in claim 1 wherein the pad comprises alginate fibres obtainable by a process comprising the following steps:
   i treating alginate fibres with a suitable acid so as to produce fibres comprising approximately 90–98% alginic acid fibres;
   ii treating the alginic acid fibres with a saturated aqueous solution of mono- or divalent cations;
   iii washing the fibres with water until imbibition of water by the fibres has effectively ceased; and iv treating the fibres with a source of a cation capable of forming a water-soluble alginate salt.

5. An autoadhesive wound dressing as claimed in claim 4 wherein the alginate fibres in i are calcium alginate.

6. An autoadhesive wound dressing as claimed in claim 4 wherein other ions and/or medicaments are included after or during step iv.

7. An autoadhesive wound dressing as claimed in claim 4 wherein the fibres comprise hyaluronic acid or a pharmaceutically acceptable salt thereof.

8. An autoadhesive wound dressing which comprises a pad of alginate fibres which fibres contain calcium ions in addition to sodium ions, the fibres being characterised by having a split maxima in the range of 100° C. to 400° C. in a plot of the first order derivative of percentage weight loss of the fibre with temperature against temperature and the dressing having a layer of pressure sensitive adhesive.

9. An autoadhesive wound dressing as claimed in claim 8 comprising a pad of alginate fibres wherein the fibres are characterised by having a Tan δ value in the range from 0 to 15 Hz.

* * * * *